(12) United States Patent
Lui et al.

(10) Patent No.: US 8,609,868 B2
(45) Date of Patent: Dec. 17, 2013

(54) PROCESS FOR PREPARING DITHIINE-TETRACARBOXY-DIIMIDES

(75) Inventors: Norbert Lui, Odenthal (DE); Jens-Dietmar Heinrich, Burscheid (DE); Thomas Himmler, Odenthal (DE); Frank Volz, Köln (DE)

(73) Assignee: Bayer CropScience AG, Monheim (DE)

( * ) Notice: Subject to any disclaimer, the term of this patent is extended or adjusted under 35 U.S.C. 154(b) by 187 days.

(21) Appl. No.: 13/101,739

(22) Filed: May 5, 2011

(65) Prior Publication Data

US 2011/0275831 A1 Nov. 10, 2011

Related U.S. Application Data

(60) Provisional application No. 61/345,268, filed on May 17, 2010.

(30) Foreign Application Priority Data

May 6, 2010 (EP) ..................................... 10162126

(51) Int. Cl.
*C07D 495/14* (2006.01)

(52) U.S. Cl.
USPC ........................................................ 548/431

(58) Field of Classification Search
CPC .................................................... C07D 495/14
USPC ........................................................ 548/431
See application file for complete search history.

(56) References Cited

U.S. PATENT DOCUMENTS

| 3,364,229 A | * | 1/1968 | Korte et al. ................... 548/431 |
| 2010/0120884 A1 | | 5/2010 | Seitz et al. |

FOREIGN PATENT DOCUMENTS

| JP | 10-251265 | 9/1998 |
| PL | 143 804 | 11/1988 |
| WO | WO 2010/043319 A1 | 4/2010 |

OTHER PUBLICATIONS

Gaina Revue Roumaine de Chimie (2005) 50 (7-8), 601-607.*
English language translation for Polish Patent Application Publication No. PL 143 804, filed Nov. 30, 1988, Patent Office of the Polish People's Republic, 6 pages.
English language translation for Japanese Patent Application Publication No. JP 10-251265, filed Sep. 22, 1998, Japanese Patent Office, 53 pages.
Draber, W., "Synthese von 1.4-Dithiinen aus Derivaten des Maleinimids," *Chem. Ber.* 100:1559-1570, Wiley-VCH, Germany (1967).
Unverified English language translation of Draber, W., "Synthesis of 1,4-Dithiins from Maleimide Derivatives," *Chem. Ber* 100:1559-1570, Deutsche Chemische Gesellschaft, Germany (1967).
Zentz, F., et al., "Syntheses, in vitro antibacterial and antifungal activities of a series of *N*-alkyl, 1,4-dithiines," *Il Farmaco* 60:944-947, Elsevier, France (2005).

* cited by examiner

*Primary Examiner* — Yong Chu
(74) *Attorney, Agent, or Firm* — Sterne, Kessler, Goldstein & Fox P.L.L.C.

(57) ABSTRACT

The present invention relates to a new process for preparing dithiine-tetracarboxy-diimides.

13 Claims, No Drawings

PROCESS FOR PREPARING DITHIINE-TETRACARBOXY-DIIMIDES

The present invention relates to a new process for preparing dithiine-tetracarboxy-diimides.

Dithiine-tetracarboxy-diimides as such are already known. It is also known that these dithiine-tetracarboxy-diimides can be used as anthelmintics against internal parasites of animals, more particularly nematodes, and have insecticidal activity (cf. U.S. Pat. No. 3,364,229). It is known, furthermore, that certain dithiine-tetracarboxy-diimides possess antibacterial activity and have a certain activity against human mycoses (cf. Il Farmaco 2005, 60, 944-947). It is also known that dithiine-tetracarboxy-diimides can be used as fungicides against phytopathogenic fungi in crop protection (cf. WO 2010/043319). It is known, furthermore, that dithiine-tetracarboxy-diimides can be used as pigments in electrophotographic photoreceptors or as dyes in paints to and polymers (cf. JP-A 10-251265, PL-B 143804).

Dithiine-tetracarboximides of the formula (I)

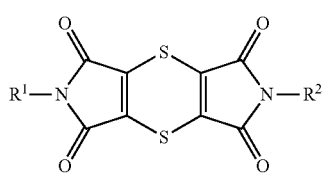

in which $R^1$ and $R^2$ are identical or different and are hydrogen, or are $C_1$-$C_8$-alkyl which is optionally substituted one or more times by halogen, —$OR^3$, and/or —$COR^4$, are $C_3$-$C_7$-cycloalkyl which is optionally substituted one or more times by halogen, $C_1$-$C_4$-alkyl or $C_1$-$C_4$-haloalkyl, or are aryl or aryl-($C_1$-$C_4$-alkyl) each of which is optionally substituted one or more times by halogen, $C_1$-$C_4$-alkyl, $C_1$-$C_4$-haloalkyl, —$COR^4$ or sulphonylamino, $R^3$ is hydrogen, $C_1$-$C_4$-alkyl or $C_1$-$C_4$-alkylcarbonyl or is aryl which is optionally substituted one or more times by halogen, $C_1$-$C_4$-alkyl or $C_1$-$C_4$-haloalkyl, $R^4$ is hydroxyl, $C_1$-$C_4$-alkyl or $C_1$-$C_4$-alkoxy, can be prepared in a variety of known ways.

For example, in one known process (cf. Synthetic Communications 2006, 36, 3591-3597), in a first stage, succinic anhydride is reacted with an amine of the formula (II), optionally in the presence of a diluent. Subsequently, the resultant succinic monoamides of the formula (III) are then reacted with a large excess of thionyl chloride in the presence of dioxane as diluent at room temperature, to give, finally, in a sequence of numerous reaction steps, the dithiine-tetracarboxy-diimides of the formula (I). The dithiine-tetracarboxy-diimides are optionally isolated directly from the reaction mixture or by filtration following addition of water. Depending on reaction conditions (diluents) and the nature of the radicals R, it is possible in certain circumstances to isolate the dithiine-diisoimides of the formula (IV) before they are converted into the dithiine-tetracarboxy-diimides of the formula (I):

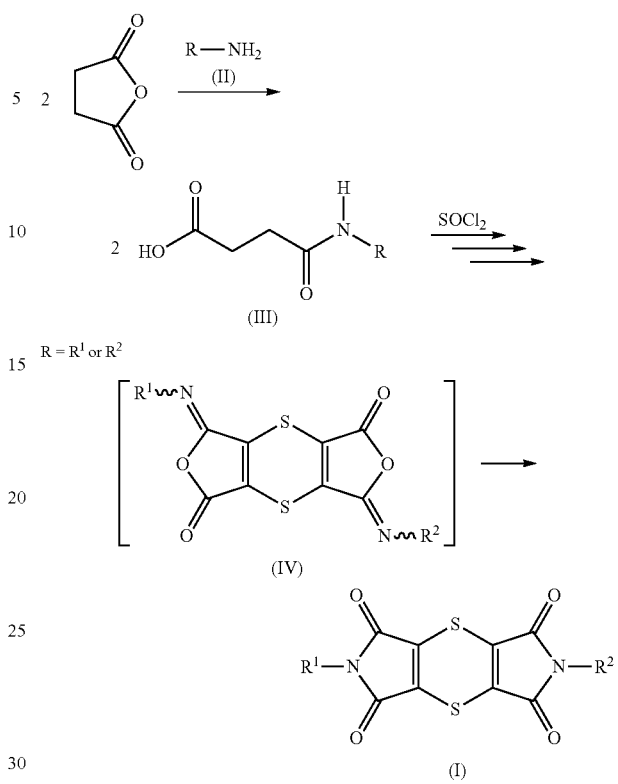

Disadvantages of this process are the long reaction time and also the outcome where either the yields obtained generally do not exceed about 30-40% of theory or else the purities of the isolated products are inadequate. A further disadvantage, in the case of aqueous work-up of the reaction mixture, is that it involves destroying large amounts of thionyl chloride; the gases formed ($SO_2$ and HCl) have to be disposed of. Likewise a disadvantage is the fact that, from experience, the product is not obtained in one portion. Instead, it is frequently the case that, following initial isolation of product by filtration, further product precipitates from the filtrate after prolonged standing (overnight, for example), and must be isolated again by filtration. Occasionally this operation must be carried out once more. This procedure is very laborious and time-consuming.

In another known process (cf. U.S. Pat. No. 3,364,229; Chem. Ber. 1967, 100, 1559-70), in a first stage, dichloromaleic anhydride of the formula (V) is reacted with an amine of formula (II), optionally in the presence of a diluent. Subsequently, the resultant dichloromaleimides of the formula (VI) are then reacted with a sulphur donor compound (for example hydrogen sulphide, thiourea or sodium thiosulphate):

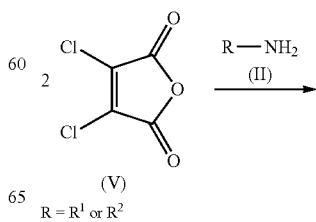

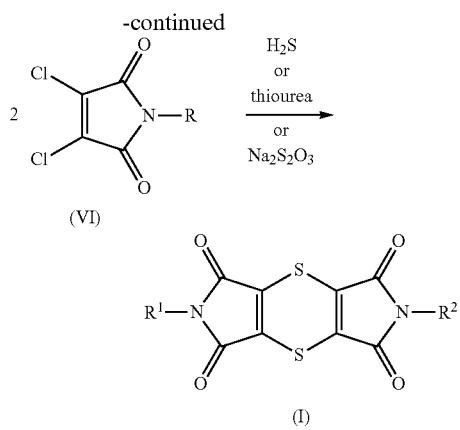

This process has the disadvantage that, for example, operating with the highly toxic gaseous hydrogen sulphide is from a technical standpoint very difficult, costly and inconvenient. When thiourea is used, in U.S. Pat. No. 3,364,229, a mixture of water and an alcohol such as, for example, methanol, ethanol and isopropanol is used. Furthermore, a mixture of acetone and water is recommended. According to the said process (Example 7), a yield of only 57% is obtained in a homogeneous mixture at reaction temperatures up to 60° C. using N-methyldichloromaleimide as starting material.

Consequently there continues to be a need for a technically simple and economic preparation process for dithiine-tetracarboxy-diimides of the formula (I).

A new process has now been found for preparing dithiine-tetracarboxy-diimides of the general formula (I)

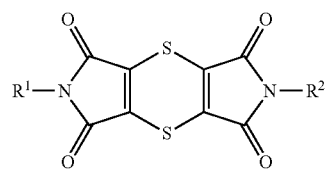

in which $R^1$ and $R^2$ have the definitions indicated above, characterized in that
dichloromaleimides of the formula (VI)

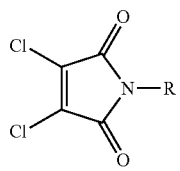

in which R is $R^1$ or $R^2$
are reacted with thiourea in water, optionally in the presence of a phase transfer catalyst, with a dichloromaleimide of the formula (VI).

A general definition of the dichloromaleimides used as starting materials when carrying out the process of the invention is provided by the formula (VI). R stands for the definitions of $R^1$ or $R^2$.

$R^1$ and $R^2$ are preferably identical or different and preferably are hydrogen, or are $C_1$-$C_6$-alkyl which is optionally substituted one or more times by fluorine, chlorine, bromine, —$OR^3$ and/or —$COR^4$, or are $C_3$-$C_7$-cycloalkyl which is optionally substituted one or more times by chlorine, methyl or trifluoromethyl, or are phenyl or phenyl-($C_1$-$C_4$-alkyl) each of which is optionally substituted one or more times by fluorine, chlorine, bromine methyl, trifluoromethyl, —$COR^4$ and/or sulphonylamino.

$R^1$ and $R^2$ are more preferably identical or different and more preferably are hydrogen, or are $C_1$-$C_4$-alkyl which is optionally substituted one or more times by fluorine, chlorine, hydroxyl, methoxy, ethoxy, methylcarbonyloxy and/or carboxyl, or are $C_3$-$C_7$-cycloalkyl which is optionally substituted one or more times by chlorine, methyl or trifluoromethyl, or are phenyl, benzyl, 1-phenethyl, 2-phenethyl or 2-methyl-2-phenethyl each of which is optionally substituted one to three times by fluorine, chlorine, bromine, methyl, trifluoromethyl, —$COR^4$ and/or sulphonylamino.

$R^1$ and $R^2$ are very preferably identical or different and very preferably are hydrogen, methyl, ethyl, n-propyl, isopropyl, 2,2-difluoroethyl or 2,2,2-trifluoroethyl or are cyclopropyl or cyclohexyl each of which is optionally substituted by chlorine, methyl or trifluoromethyl.

$R^1$ and $R^2$ are more particularly preferably simultaneously methyl.

$R^3$ is preferably hydrogen, methyl, ethyl, methylcarbonyl or ethylcarbonyl or is phenyl which is optionally substituted one or more times by fluorine, chlorine, methyl, ethyl, n-propyl, isopropyl or trifluoromethyl.

$R^3$ is more preferably hydrogen, methyl, methylcarbonyl or phenyl.

$R^4$ preferably is hydroxyl, methyl, ethyl, methoxy or ethoxy.

$R^4$ is more preferably hydroxyl or methoxy.

As starting material it is particularly preferred to use N-methyldichloromaleimide (VI-1), R=Me, giving as the end product the compound (I-1) 2,6-dimethyl-1H,5H-[1,4]dithiino[2,3-c:5,6-c']dipyrrole-1,3,5,7(2H,6H)-tetrone.

If dichloromaleimide (VI-2), R=H is used as starting material, the compound (I-2) 1H,5H-[1,4]dithiino[2,3-c:5,6-c']dipyrrole-1,3,5,7(2H,6H)tetrone is obtained as end product.

The process of the invention does not require any organic solvent which needs to be disposed of or recovered at the end of the reaction, and achieves relatively high yields.

The thiourea is used in amounts between 0.8 and 2 mol per mole of dichloromaleimide of the formula (VI). Preferred amounts are between 0.9 and 1.7 mol of thiourea, more preferably between 1.0 and 1.3 mol of thiourea, per mole of dichloromaleimide of the formula (VI).

The thiourea can be added to the reaction mixture in solid form or as a solution/suspension in water. It is preferred to initially charge the thiourea in water.

The reaction temperature in the process of the invention can be varied within wide limits and lies between 40° C. and 150° C. In order to obtain satisfactory space-time yields, it is preferred to operate at temperatures between 50° C. and 120° C., more preferably between 60° C. and 100° C.

The dichloromaleimide of the formula (VI) is metered preferably at temperatures from 60° C. to 90° C. into the aqueous solution.

In the case of the reaction in water, a phase transfer catalyst (PTC) may optionally be added. As phase transfer catalysts it is possible in principle to use all compounds possessing known activity as PTCs. Such compounds may be, for example, phase transfer catalysts from the series of the quaternary ammonium salts or of the quaternary phosphonium salts.

This phase transfer catalyst preferably possesses the general formula (VII)

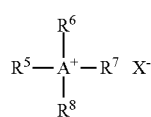

in which
A is N or P,
$R^5$, $R^6$, $R^7$ and $R^8$ are identical or different and independently are branched or unbranched $C_1$-$C_{28}$-alkyl, $C_6$-$C_{10}$-aryl or benzyl,
X is halogen, hydrogen sulphate, sulphate, dihydrogen phosphate, hydrogen phosphate, phosphate or acetate.
X preferably is bromine, chlorine, fluorine, hydrogen sulphate, sulphate, phosphate and acetate.

Examples that may be given of phase transfer catalysts of the formula (VII) include the following: benzyltributylammonium bromide, benzyltributylammonium chloride, benzyltriethylammonium bromide, benzyltriethylammonium chloride, benzyltrimethylammonium chloride, cetyltrimethylammonium bromide, didecyldimethylammonium chloride, dimethyldistearylammonium bisulphate, dimethyldistearylammonium methosulphate, dodecyltrimethylammonium bromide, dodecyltrimethylammonium chloride, methyltributylammonium chloride, methyltributylammonium hydrogen sulphate, methyltricaprylylammonium chloride, methyltrioctylammonium, chloride, myristyltrimethylammonium bromide, phenyltrimethylammonium chloride, tetrabutylammonium chloride, tetrabutylammonium fluoride, tetrabutylammonium bromide, tetrabutylammonium hydrogen sulphate, tetrabutylammonium hydroxyide, tetrabutylammonium iodide, tetraethylammonium bromide, tetraethylammonium chloride, tetraethylammonium hydroxide, tetrahexylammonium bromide, tetrahexylammonium iodide, tetramethylammonium bromide, tetramethylammonium chloride, tetramethylammonium fluoride, tetramethylammonium hydroxide, tetramethylammonium iodide, tetraoctylammonium bromide, tetrapropylammonium bromide, tetrapropylammonium chloride, tetrapropylammonium hydroxide, tributylmethylammonium chloride, triethylbenzylammonium chloride, tetraphenylphosphonium bromide, ethyl-tiphenylphosphonium bromide, ethyltriphenylphosphonium iodide and ethyltriphenylphosphonium acetate, and mixtures of these.

It is also possible, furthermore, for phase transfer catalysts such as 4-dialkylaminopyridinium salts or hexaalkyl-guanidinium salts to be employed.

The phase transfer catalyst may be used in the range from 0.1 to 20 mol %, based on the dichloromaleiimide of the formula (VI).

The reaction time in the process of the invention is between 15 minutes and 24 hours. It is preferred to operate for between 30 minutes and 12 hours, more preferably between 1 and 6 hours.

The workup of the product is carried out by filtration.

The process of the invention is illustrated by, but not confined to, the following examples.

COMPARATIVE EXAMPLE 1

The comparative example is carried out in accordance with Chemische Berichte [Chemical Reports] 1967, 100, 1559-1570 (page 1566, Method B).

A solution of 9 g (0.05 mol) of N-methyldichloromaleimide in 50 g of water was introduced and, over the course of 60 minutes, a 10% aqueous thiourea solution was added dropwise at 40° C. Subsequently, the mixture was stirred at 40° C. for 5 hours. Thereafter the reaction mixture was cooled to 10° C., and the solid was isolated by filtration with suction, washed with in each case 20 ml of water and then 20 ml of MeOH, and dried. This gave 3.7 g of green solid, which according to HPLC analysis is composed to an extent of 75.8 area-% of the compound (I-1), corresponding to a yield of 38.8% of theory.

EXAMPLE 1

An amount of 4.2 g (0.055 mol) of thiourea was introduced in 100 g of water. Subsequently 1.6 g of tetrabutylammonium bromide were added and the mixture was heated to 80° C. Subsequently 9 g (0.05 mol) of N-methyldichloromaleiimide were added. The reaction mixture was then stirred at 80° C. for 2 hours. Thereafter it was cooled to 20° C., and the solid was isolated by filtration with suction, washed with 20 ml of water and then with 20 ml of MeOH, and dried. This gave 6.5 g of green solid, which according to HPLC analysis is composed to an extent of 93% (against standard) of the compound (I-1), corresponding to a yield of 85.3% of theory.

EXAMPLE 2

An amount of 4.2 g (0.055 mol) of thiourea was introduced in 100 g of water and the solution was heated to 80° C. Subsequently 9 g (0.05 mol) of N-methyldichloromaleiimide were added. The reaction mixture was then stirred at 80° C. for 2 hours. Thereafter it was cooled to 20° C., and the solid was isolated by filtration with suction, washed with 20 ml of water and then with 20 ml of MeOH, and dried. This gave 6.02 g of green solid, which according to to HPLC analysis is composed to an extent of 94.3% (against standard) of the compound (I-1), corresponding to a yield of 80.6% of theory.

EXAMPLE 3

An amount of 4.2 g (0.055 mol) of thiourea was introduced in 100 g of water. Subsequently 0.8 g of tetrabutylammonium bromide were added and the mixture was heated to 80° C. Subsequently 9 g (0.05 mol) of N-methyldichloromaleiimide was added. The reaction mixture was then stirred at 80° C. for 2 hours. Thereafter it was cooled to 20° C., and the solid was isolated by filtration with suction, washed with 20 ml of water and then with 20 ml of MeOH, and dried. This gave 6.2 g of green solid, which according to HPLC analysis is composed to an extent of 94.3% (against standard) of the compound (I-1), corresponding to a yield of 82.6% of theory.

EXAMPLE 4

An amount of 4.2 g (0.055 mol) of thiourea was introduced in 100 g of water. Subsequently 0.15 g of tetrabutylammonium bromide was added and the mixture was heated to 80° C. Subsequently 9 g (0.05 mol) of N-methyldichloromaleiimide were added. The reaction mixture was then stirred at 80° C. for 2 hours. Thereafter it was cooled to 20° C., and the solid was isolated by filtration with suction, washed with 20 ml of water and then with 20 ml of MeOH, and dried. This gave 5.94 g of green solid, which according to HPLC analysis is composed to an extent of 91.4% (against standard) of the compound (I-1), corresponding to a yield of 81% of theory.

EXAMPLE 5

An amount of 4.2 g (0.055 mol) of thiourea was introduced in 100 g of water. Subsequently 0.38 g of methyltri-n-octylammonium chloride was added and the mixture was heated to 80° C. Subsequently 9 g (0.05 mol) of N-methyldichloromaleiimide were added. The reaction mixture was then stirred at 80° C. for 2 hours. Thereafter it was cooled to 20° C., and the solid was isolated by filtration with suction, washed with 20 ml of water and then with 20 ml of MeOH, and dried. This gave 5.8 g of green solid, which according to HPLC analysis is composed to an extent of 94.7 area-% of the compound (I-1), corresponding to a yield of 82.1% of theory.

The invention claimed is:

1. A process for preparing a compound of general formula (I)

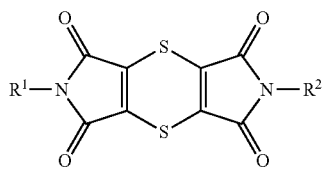

in which
$R^1$ and $R^2$ are identical or different and are selected from the group consisting of hydrogen; $C_1$-$C_8$-alkyl, which is optionally substituted one or more times by halogen, —$OR^3$, or —$COR^4$; $C_3$-$C_7$-cycloalkyl, which is optionally substituted one or more times by halogen, $C_1$-$C_4$-alkyl or $C_1$-$C_4$-haloalkyl; and aryl or aryl-($C_1$-$C_4$-alkyl), each of which is optionally substituted one or more times by halogen, $C_1$-$C_4$-alkyl, $C_1$-$C_4$-haloalkyl, —$COR^4$ or sulphonylamino,
$R^3$ is hydrogen, $C_1$-$C_4$-alkyl, $C_1$-$C_4$-alkylcarbonyl or is aryl which is optionally substituted one or more times by halogen, $C_1$-$C_4$-alkyl or $C_1$-$C_4$-haloalkyl,
$R^4$ is hydroxyl, $C_1$-$C_4$-alkyl or $C_1$-$C_4$-alkoxy,
wherein
a compound of formula (VI)

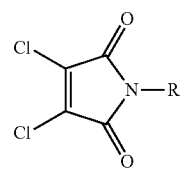

in which R is $R^1$ or $R^2$ is reacted with thiourea in water, optionally in the presence of a phase transfer catalyst, in the absence of an organic solvent to give the compound of formula (I).

2. A process according to claim 1, wherein the compound of formula (VI) is reacted with thiourea in the presence of a phase transfer catalyst of formula (VII)

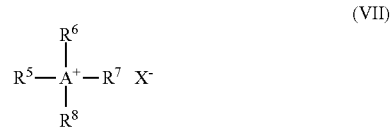

in which
A is N or P,
$R^5$, $R^6$, $R^7$ and $R^8$ are identical or different and are independently branched or unbranched $C_1$-$C_{28}$-alkyl, $C_6$-$C_{10}$-aryl or benzyl,
X is halogen, hydrogen sulphate, sulphate, dihydrogen phosphate, hydrogen phosphate, phosphate or acetate.

3. A process according to claim 1, wherein between 0.8 and 2 mol of thiourea are used per mole of the compound of formula (VI).

4. A process according to claim 1, wherein between 0.9 and 1.7 mol of thiourea are used per mole of the compound of formula (VI).

5. A process according to claim 1, wherein between 1.0 and 1.3 mol of thiourea are used per mole of the compound of formula (VI).

6. A process according to claim 1, wherein the thiourea is initially introduced in water.

7. A process according to claim 2, wherein between 0.8 and 2 mol of thiourea are used per mole of the compound of formula (VI).

8. A process according to claim 2, wherein between 0.9 and 1.7 mol of thiourea are used per mole of the compound of formula (VI).

9. A process according to claim 2, wherein between 1.0 and 1.3 mol of thiourea are used per mole of the compound of formula (VI).

10. A process according to claim 2, wherein the thiourea is initially introduced in water.

11. A process according to claim 3, wherein the thiourea is initially introduced in water.

12. A process according to claim 4, wherein the thiourea is initially introduced in water.

13. A process according to claim 5, wherein the thiourea is initially introduced in water.

* * * * *